US008506619B2

(12) United States Patent
Ortiz et al.

(10) Patent No.: US 8,506,619 B2
(45) Date of Patent: *Aug. 13, 2013

(54) VARIABLE DENSITY BRAID STENT

(75) Inventors: John Ortiz, East Palo Alto, CA (US);
Masoud Molaei, Fremont, CA (US);
Frank Musbach, Pleasanton, CA (US);
Brent C. Gerberding, Sunnyvale, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 224 days.

This patent is subject to a terminal disclaimer.

(21) Appl. No.: 12/836,357

(22) Filed: Jul. 14, 2010

(65) Prior Publication Data
US 2010/0280587 A1 Nov. 4, 2010

Related U.S. Application Data

(63) Continuation of application No. 10/744,533, filed on Dec. 22, 2003, now Pat. No. 7,763,011.

(51) Int. Cl.
*A61F 2/06* (2013.01)
(52) U.S. Cl.
USPC ........................................ 623/1.16
(58) Field of Classification Search
USPC ................................ 623/1.11–1.54
See application file for complete search history.

(56) References Cited

U.S. PATENT DOCUMENTS

| | | | |
|---|---|---|---|
| 4,655,771 A | 4/1987 | Wallsten | |
| 5,061,275 A | 10/1991 | Wallsten et al. | |
| 5,354,295 A | 10/1994 | Guglielmi et al. | |
| 5,449,372 A | 9/1995 | Schmaltz | |
| 5,817,126 A * | 10/1998 | Imran | 623/1.15 |
| 5,836,966 A | 11/1998 | St. Germain | |
| 5,849,037 A | 12/1998 | Frid | |
| 5,855,600 A | 1/1999 | Alt | |
| 5,902,317 A | 5/1999 | Kleshinski et al. | |
| 5,913,895 A | 6/1999 | Burpee et al. | |
| 5,922,021 A | 7/1999 | Jang | |
| 5,938,697 A | 8/1999 | Killion et al. | |
| 6,132,461 A | 10/2000 | Thompson | |

(Continued)

FOREIGN PATENT DOCUMENTS

| | | |
|---|---|---|
| EP | 0897698 | 2/1999 |
| WO | 98/47447 | 10/1998 |

(Continued)

*Primary Examiner* — David Isabella
*Assistant Examiner* — Ann Schillinger
(74) *Attorney, Agent, or Firm* — Vista IP Law Group LLP

(57) ABSTRACT

A stent comprises at least one stent member woven to form a substantially tubular body that defines a flow path. The tubular body comprises a first region and a second region. In the first region the at least one stent member defines a plurality of first region openings and in the second region at least one first portion of the at least one member and at least one second portion of the at least one member are engaged together to form at least one primary strand. The at least one primary strand defines a plurality of second region openings. The at least one of the plurality of second region openings is in fluid communication with the flow path. The plurality of second region openings provide the second region with a greater porosity than the first region.

14 Claims, 2 Drawing Sheets

(56) References Cited

U.S. PATENT DOCUMENTS

| | | |
|---|---|---|
| 6,146,403 A | 11/2000 | St. Germain |
| 6,159,238 A | 12/2000 | Killion et al. |
| 6,179,867 B1 | 1/2001 | Cox |
| 6,258,115 B1 | 7/2001 | Dubrul |
| 6,273,910 B1 | 8/2001 | Limon |
| 6,273,911 B1 | 8/2001 | Cox et al. |
| 6,315,792 B1 | 11/2001 | Armstrong et al. |
| 6,371,982 B2 | 4/2002 | Berg et al. |
| 6,398,807 B1 | 6/2002 | Chouinard et al. |
| 6,409,754 B1 | 6/2002 | Smith et al. |
| 6,423,084 B1 | 7/2002 | St. Germain |
| 6,423,090 B1 | 7/2002 | Hancock |
| 6,461,380 B1 | 10/2002 | Cox |
| 6,468,302 B2 | 10/2002 | Cox et al. |
| 6,485,509 B2 | 11/2002 | Killion et al. |
| 6,511,505 B2 | 1/2003 | Cox et al. |
| 6,565,602 B2 | 5/2003 | Rolando et al. |
| 6,585,758 B1 | 7/2003 | Chouinard et al. |
| 6,602,284 B2 | 8/2003 | Cox et al. |
| 6,610,087 B1 | 8/2003 | Zarbatany et al. |
| 6,616,689 B1 | 9/2003 | Ainsworth et al. |
| 6,629,994 B2 | 10/2003 | Gomez et al. |
| 6,652,572 B2 | 11/2003 | Kugler et al. |
| 6,652,576 B1 | 11/2003 | Stalker |
| 7,172,617 B2 | 2/2007 | Colgan et al. |
| 2003/0195609 A1 | 10/2003 | Berenstein et al. |
| 2004/0010307 A1* | 1/2004 | Grad et al. .................... 623/1.15 |
| 2004/0106985 A1* | 6/2004 | Jang ............................. 623/1.16 |

FOREIGN PATENT DOCUMENTS

| | | |
|---|---|---|
| WO | 01/0012 A1 | 1/2001 |
| WO | 02/15824 | 2/2002 |
| WO | 2004/045461 | 6/2004 |

* cited by examiner

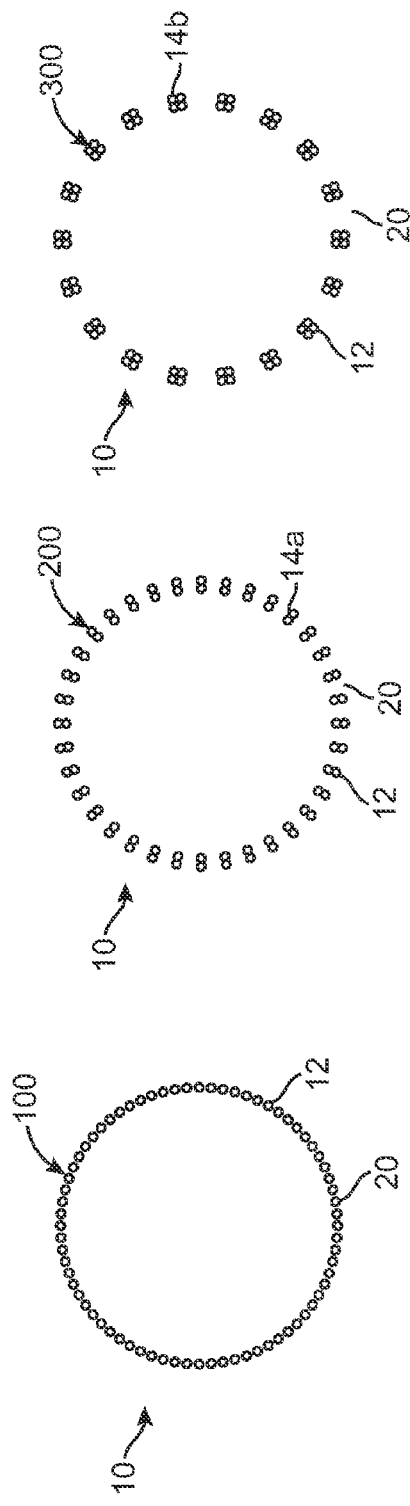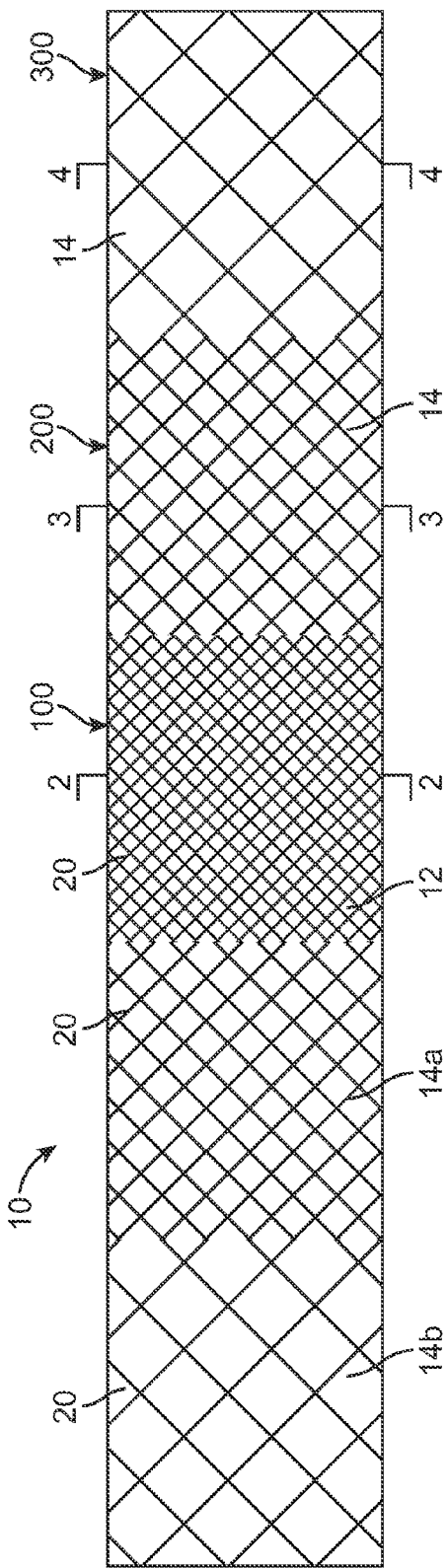

VARIABLE DENSITY BRAID STENT

CROSS-REFERENCE TO RELATED APPLICATIONS

This application is a continuation application of co-pending U.S. patent application Ser. No. 10/744,533, filed Dec. 22, 2003, the priority of which is claimed under 35 U.S.C. §120, and the contents of which are incorporated herein by reference as though set forth in full.

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, mechanically expandable or hybrid expandable.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy, nickel, titanium, nitinol, platinum, chrome cobalt alloy, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern.

Some examples of stents or stent components that may be braided are described in U.S. Pat. No. 5,061,275, U.S. Pat. No. 4,655,771, U.S. Pat. No. 6,146,403, U.S. Pat. No. 5,836,966, U.S. Pat. No. 642,308, as well as in U.S. application Ser. No. 10/063,315 to Eder et al., filed Apr. 10, 2002.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to expand to a predetermined diameter in the vessel.

Despite the wide variety of stents presently available, there remains a desire to provide a braided stent, particularly one suitable for use in neuro-vasculature applications and/or other applications, having a variable porosity wherein a portion of the stent has sufficient porosity to allow diffusion of body fluids to those vessels, including small vessels known as perforators, that intersect or are adjacent to the deployed stent, but also a porosity which is constructed and arranged to occlude at the neck of an aneurysm and/or areas adjacent thereto.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In light of the above the present invention is directed to a variety of embodiments. For example, in at least one embodiment the invention is directed to a braided stent having a variable porosity along the length of the stent. The variability of the porosity is provided to the stent in a variety of ways. For example, in some embodiments the stent is constructed from a plurality or fibers, wires, or other members which are distributed in different manners along the length of the stent. One or more members may be selectively braided into one or more strands.

In some embodiments the members may be woven or braided into other composite members or strands. In some embodiments the members may be woven together in tighter or looser patterns to provide a given area of the stent a greater or lesser concentration of stent material as may be desired. By varying the distribution of the stent members in any of a variety of manners, the spaces or pores of the stent defined by the members may be provided with a wide range of shapes and sizes depending on the number and distribution pattern of the members in a particular portion of the stent.

In some embodiments the members may be selectively braided together to form one or more individual strands comprised of any number of a plurality of members. Any given portion of the stent may be constructed of individual members, strands or a combination thereof.

A strand may have any number of members that are woven or otherwise bound together. By varying the number of members in different portion of the stent, such as by incorporating the members into one or more strands or by freeing members that were incorporated into one or more strands, the number of spaces between adjacent members and/or strands is reduced or increased respectively. However, because the concentration of the stent spaces may be modified by varying the weave of the stent members and/or strands, in some embodiments by selectively modifying the weave of the stent, the change in space concentration (porosity) resulting from forming members into strands and/or freeing members from existing strands, may be enhanced or compensated for as desired.

The number and distribution of members and/or strands may also affect the size and shape of the openings between adjacent members and/or strands. In some embodiments for example where the stent has a set number of members, as members are incorporated into one or more strands, the number of openings between the members/strands will decrease and the size of those openings remaining will typically be larger. Inversely, unraveling or freeing members from one or more of the strands will result in an increase in the number of openings and the openings will typically be of a smaller size. As indicated above, selectively modifying the weave of the stent may allow the change in size, shape and number of spaces to be enhanced or compensated for as desired.

In at least one embodiment a stent is provided with a plurality of members in a first portion of the stent. The members are formed into a plurality of strands into one or more portions of the stent adjacent to the first portion of the stent. In at least one embodiment a stent is provided with a predetermined number of members in at least one first portion of the stent. In at least one portion of the stent adjacent to the at least one first portion, the predetermined number of members is formed into a predetermined number of strands. In some embodiments the predetermined number of strands is a number which is a fraction of the predetermined number of members. In some embodiments the predetermined number of members is a multiple of the predetermined number of strands. In some embodiments the predetermined number of members is an even multiple of the predetermined number of strands. In some embodiments the predetermined number of members is an odd multiple of the predetermined number of strands.

In at least one embodiment the predetermined number of members defines a first predetermined number of stent spaces for a given area of the stent made up of stent members and the predetermined number of strands defines a second predetermined number of stent spaces for a given area of the stent made up of strands. In some embodiments the first predetermined number of stent spaces is different than the second predetermined number of stent spaces. In some embodiments the first predetermined number of stent spaces is greater than the second predetermined number of stent spaces.

In at least one embodiment a stent is provided with at least one portion having a first predetermined number of strands. At least one portion of the stent adjacent thereto comprises a second predetermined number of strands. In some embodiments the first predetermined number of strands is different than the second predetermined number of strands. In some embodiments the first predetermined number of strands is a multiple of the second predetermined number of strands. In some embodiments the first predetermined number of strands is an even multiple of the second predetermined number of strands. In some embodiments the first predetermined number of strands is an odd multiple of the second predetermined number of strands.

In at least one embodiment the weave angle between adjacent members and/or strands is substantially same throughout the stent. In some embodiments the weave angle between adjacent members and/or strands in different portions of the stent may be different.

In at least one embodiment one or more members of a stent are at least partially constructed from a shape memory material such as a shape memory polymer, metal or any combination thereof. In some embodiments one or more of the members are at least partially constructed of nitinol, stainless steel, Elgiloy, and any combination or alloy thereof.

In at least one embodiment of the invention one or more members of a stent is at least partially constructed from a radiopaque material such as gold, platinum, chrome cobalt alloy, etc.

In at least one embodiment, one or more portions of the stent is balloon expandable, self-expandable and/or hybrid expandable.

In at least one embodiment the members and/or strands define a plurality of openings, wherein the area of each of the openings is about 0.0005 mm$^2$ to about 0.55 mm$^2$ or more. In some embodiments at least one portion of the stent is constructed and arranged to be positioned over an aneurysm, and at least one portion of the stent may be constructed and arranged to be positioned adjacent to a blood vessel. In some embodiments the portion of the stent constructed and arranged for placement of the aneurysm comprises a plurality of openings wherein each opening has an area of about 0.0005 mm$^2$ to about 0.25 mm$^2$. In some embodiments the portion of the stent constructed and arranged to be positioned adjacent to a blood vessel comprises a plurality of openings wherein each opening has an area of about 0.005 mm$^2$ to about 0.55 mm$^2$ or greater.

In at least one embodiment a stent is comprised of one or more members. In some embodiments the stent is comprised of at least 18 members. In some embodiments the stent is comprised of at least 36 members. In some embodiments the stent is comprised of at least 72 members or more.

In at least one embodiment where the stent is comprised of 72 members, at least one portion of the stent is constructed of the 72 members, and at least one first portion of the stent adjacent thereto is constructed of a number of strands derived from the members, such that the at least one adjacent portion comprises between 1 and 36 primary strands. In some embodiments at least one second portion of the stent adjacent to the at least one first portion is constructed of a number of secondary strands derived from the primary strands, such that the at least one secondary portion comprises between 1 and 18 secondary strands. In some embodiments a stent may be provided with portions which comprise different numbers of strands and/or portions having strands of different member density (e.g. the number of members a given strand is comprised of). In some embodiments the member density of the strands in a given portion of the stent may be substantially the same or different from one another.

In at least one embodiment the number of members that a given strand may be constructed from is 2 members to about 16 members.

In at least one embodiment the members of a stent have a cross-sectional diameter of about 0.0005 inch to about 0.002 inch. In at least one embodiment the cross-sectional thickness of one or more of the members of the stent may be varied.

In at least one embodiment the stent is at least partially constructed from and/or coated with one or more polymer materials.

In at least one embodiment the stent is provided with a biocompatible coating.

In at least one embodiment the stent is constructed and arranged to deliver one or more therapeutic agents.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL
VIEWS OF THE DRAWING(S)

A detailed description of the invention is hereafter described with specific reference being made to the drawings.

FIG. 1 is a side view of an embodiment of the invention.

FIG. 2 is a cross-sectional view corresponding to section line '2' of the embodiment shown in FIG. 1.

FIG. 3 is a cross-sectional view corresponding to section line '3' of the embodiment shown in FIG. 1.

FIG. 4 is a cross-sectional view corresponding to section line '4' of the embodiment shown in FIG. 1.

DETAILED DESCRIPTION OF THE INVENTION

Figure 5:
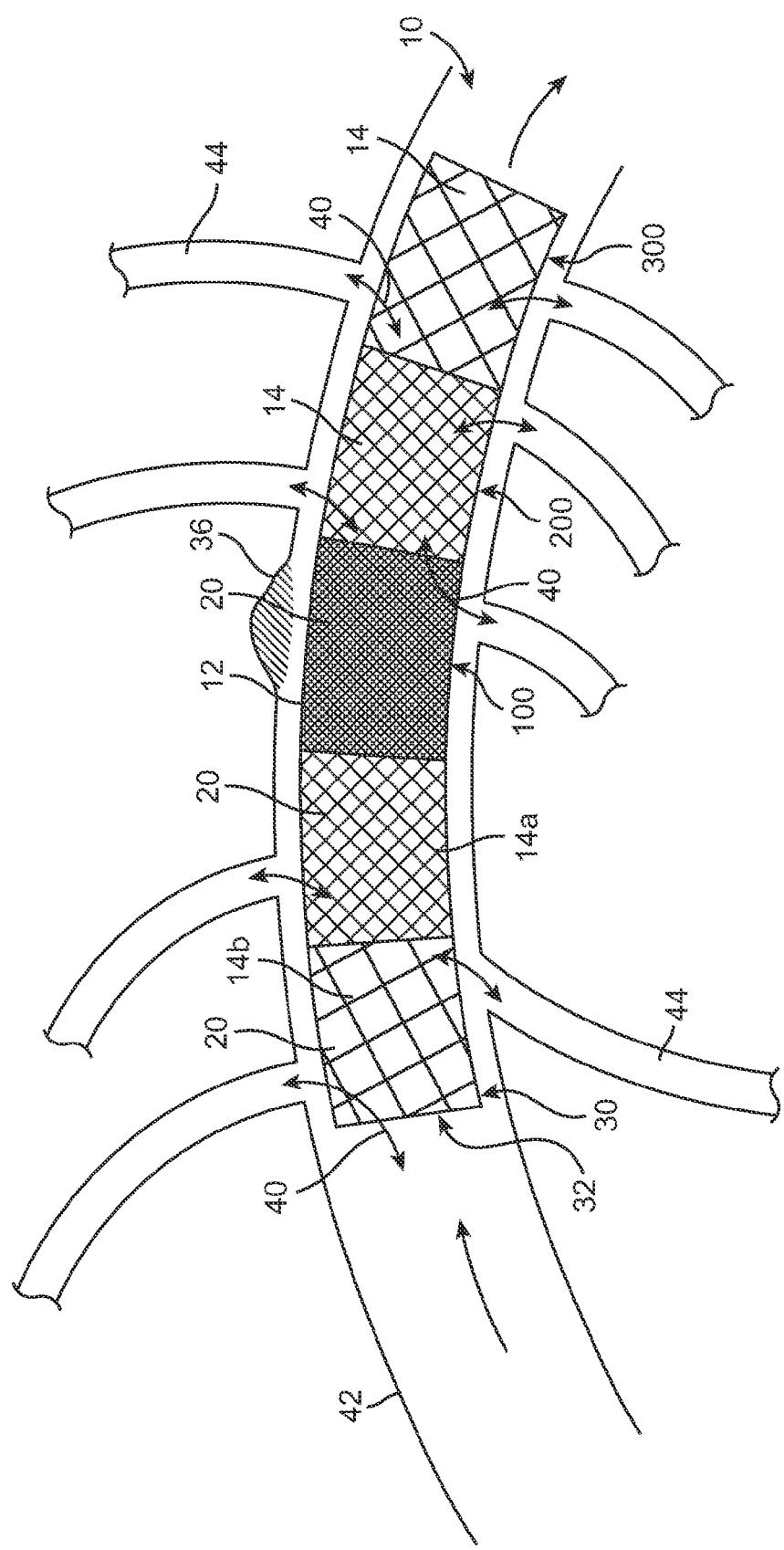
FIG. 5 is a longitudinal cross-sectional view of an embodiment of the invention shown positioned within a body lumen.

While this invention may be embodied in many different forms, there are described in detail herein embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, the invention may be embodied in a variety of forms. In at least one embodiment, an example of which is depicted in FIGS. 1-4, the invention is directed to a stent 10 that is comprised of members 12 that are selectively woven into one or more strands 14 in order to provide the stent 10 with portions or regions, which may have different porosity characteristics from one another. In the various figures strands are generally indicated at 14, an additional letter designation such as 14a and 14b, is used to indicate strands of different regions of the stent 10.

The term 'porosity' as used herein refers to the ability of the openings 20 in a given region of the stent to pass bodily fluids, such as blood, therethrough. For example, in the embodiment shown in FIG. 1, a stent 10 has at least three regions 100, 200, and 300 of different porosity. Each of the regions has a different number of openings 20 over substantially similar lengths of the stent 10. In the embodiment shown the openings 20 in each region are also of a particular size which may also be different in different regions 100, 200 and 300. It should be noted that in alternative embodiments the openings 20 may vary in size in a particular region depending on the spacing, concentration and braid characteristics of the members 12 and/or strands 14. The differences in the characteristics of the openings 20 in each region 100, 200 and 300 provide each region with a different porosity. Though a region, such as region 100 may have more openings than an adjacent region 200 or 300, the porosity of the regions 200 and/or 300 is greater than that of region 100 as one or more of the openings 20 in regions 200 and/or 300 are sized to allow body fluid to pass therethrough, where as the more numerous openings 20 in region 100 are more restrictive.

In the embodiment shown in FIG. 1, the porosity of the regions 100, 200 and 300 is altered as a result of the change in the relative position and distribution of the members 12 as they are braided into the strands 14 of region 200 and as the strands 14a of region 200 are further braided into the strands 14b of region 300, such as in the manner illustrated in FIGS. 2-4.

In order to illustrate the different porosity and weave density between regions 100, 200 and 300, the embodiment of the stent 10 shown in FIGS. 1-4 are depicted with a somewhat simplified braid pattern. One or ordinary skill will recognize that in some embodiments the stent 10 will not have the distinct and precisely separated braid patterns shown in the respective regions 100, 200 and 300, but will include transition regions wherein the pattern and density of the strands 14 and/or members 12 will be 'in between' that depicted in the various figures. Such transition regions do not interfere with the desired porosity characteristics of the regions 100, 200 and 300 as described herein.

As is shown in FIGS. 1 and 2, in region 100 the members 12 are substantially uniformly positioned about the circumference of the stent 10 to provide the stent 10 with a first porosity. In order to provide the region 100 with a uniform porosity throughout the region 100 the members 12 are uniformly distributed about the circumference of the stent 10. In alternative embodiments however, the members 12 may be arranged in any manner desired to provide a variable porosity within the region 100.

As the members 12 extend toward region 200, they are selectively braided together or otherwise engaged to form primary or first strands 14a. In the embodiment shown in FIGS. 1 and 3, each first strand 14a is comprised of at least two members 12 which are braided together by interweaving adjacent members 12 about one another. As indicated above however, other mechanisms for forming strands 14a may be used as well. The second region 200 may comprise any number of strands 14a having any concentration of members 12. However, where it is desired to provide region 200 with a uniform porosity then the distribution of members 12 into strands 14a should be uniform about the circumference of the region 200. It should further be noted that in some embodiments one or more members 12 may remain separate or unbraided within the regions 200 and/or 300.

As the first or primary strands 14a of region 200 extend toward region 300, the strands 14a are further selectively braided or otherwise engaged together to form secondary strands 14b such as are shown in FIGS. 1 and 4. Each secondary strand 14b is constructed by engaging at least two adjacent primary strands 14a together. In the embodiment shown in FIG. 4 each secondary strand 14b is constructed by interweaving adjacent primary strands 14a about one another. The third region 300 may comprise any number of secondary strands 14b having any concentration of primary strands 14a or members 12. However, where it is desired to provide region 300 with a uniform porosity then the distribution of members 12 and/or primary strands 14a into secondary strands 14b should be uniform about the circumference of the region 300. It should further be noted that in some embodiments one or more members 12 and/or one or more secondary strands 14a may remain separate or unbraided within the region 300.

As is shown in FIG. 5, the stent 10 is provided with a substantially mesh-like tubular body 30 that defines a flow path 32 therethrough. However, because the regions 100, 200 and 300 of the stent are provided with different porosities as a result of the selective braiding of the members 12 into strands 14, the flow characteristics of blood and other body fluids, indicated by arrows 40 through the openings 20 will be different in the different regions of the stent 10.

For example, in the embodiment shown in FIG. 5, when the stent 10 is positioned within a body lumen or vessel 42, the stent 10 is deployed so that the region 100 occludes an aneurysm 36, within the vessel 42. It should be noted however that aneurysm 36 may be any sort of lesion, stenosis or defect within the vessel 42.

The size of the openings 20 of the first region 100 is sufficiently small so as to restrict blood 40 through the openings 20 causing stagnation in the area of the aneurysm 36. However, by providing the stent 10 with other regions, adjacent to the first region 100, which have a porosity characterized by openings 20 of a greater size, one or more of the regions 200 and 300 will allow blood 40 to flow through the openings 20 therein. By providing one or more regions 200 and 300 with sufficient porosity to allow blood flow therethrough, such regions may cross over or intersect branch vessels or perforators 44 of the primary vessel 42 without significantly interfering with the flow of blood 40 therebetween. As a result, of the different porosities provided to the stent 10 blood flow to the aneurysm 36 is prevented or restricted, while flow to adjacent perforators or other vessels is maintained.

In some embodiments, the porosity of region 100 may be characterized such that blood flow 40 to the area of the aneurysm 36 will stagnate but will be able to flow through the openings 20 to one or more perforators 44 adjacent thereto.

In at least one embodiment each opening 20 of the first region 100 has an area of about 0.0005 mm$^2$ to about 0.25 mm$^2$. In at least one embodiment each opening 20 of the second region 200 and/or the third region 300 has an area of about 0.005 mm$^2$ to about 0.55 mm$^2$. Where the stent 10 has both region 200 and region 300 typically the openings 20 in region 300 will each have a greater area than those in the region 200.

In at least one embodiment of the invention, in a given region of the of the stent 10, as the number of members 12 present in each strand 14 increases, the number of openings in a given region will decrease and their respective size will increase. Though such a stent 10 is provided with one or more regions of increased porosity, such regions are not structurally compromised or less resistant to compression in the expanded state because as the size of the openings increase the relative strength of each strand 14 defining the openings 20 will also increase as the number of members 12 braided together are increased.

In at least one embodiment each member 12 of the stent 10 have a cross-sectional diameter of about 0.0005 inch to about 0.002 inch.

It should be understood that the stent 10 illustrated in FIGS. 1-5 is representative of a single embodiment of the present invention. The stent 10 may have any number of regions defined by different strand thickness and/or porosity. A given region may be comprised of one or more strands 14 or members 12 arranged in any pattern desired.

In the various embodiments shown in FIGS. 1-5, the stent 10, or one or more portions thereof may be balloon expandable, self-expandable and/or hybrid expandable. In at least one embodiment, at least one of the regions 100, 200 and/or 300 of the stent 10 is balloon expandable, whereas at least one of the remaining regions is self-expandable. The stent 10 may be constructed of any of variety of suitable stent materials such as stainless steel, Elgiloy, nickel, titanium, platinum, chrome, cobalt, as well as other metals, alloys and combinations thereof. In at least one embodiment one or more of the members 12 are at least partially constructed from nitinol. In at least one embodiment one or more of the members 12 are at least partially constructed from a shape memory polymer. In at least one embodiment one or more members 12 and/or strands 14 are constructed of a radiopaque material such as platinum, gold, chrome-cobalt, etc.

In some embodiments the stent 10, or one or more portions thereof, may be configured to deliver one or more therapeutic agents to the aneurysm 36. One or more members 12 and/or strands 14 maybe configured to include one or more holes, notches, or other surface features to which one or more therapeutic agents may be placed for delivery to the aneurysm site. A therapeutic agent may be placed on the stent in the form of a coating. In at least one embodiment the coating includes at least one therapeutic agent and at least one polymer.

A therapeutic agent may be a drug, a non-genetic agent, a genetic agent, etc. Some examples of suitable non-genetic therapeutic agents include but are not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, growth factor receptor agonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, including (cells and/or cell fragments), the cellular material may include but is not limited to: cells of human origin (autologous or allogeneic); cells of non-human origin (xenogeneic) and any combination thereof.

Where a therapeutic agent comprises at least one polymer coating or carrier, the at least one coating or carrier may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate; polyhydroxyvalerate; coatings from polymer dispersions such as polyurethane dispersions (BAYHDROL®, etc.), fibrin, elastin, fibrinogen, fibronectin, vitronectin, laminin, silk, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; poly amino acid; polyphosphazenes; polyiminocarbonates; polyhydroxyalkanoates; polydimethyltrimethylcarbonates; biodegradable $CA/PO_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations, blends and/or copolymers thereof.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent for insertion into a patient blood vessel having an aneurysm, the stent comprising:
   a substantially tubular body defining a flow path therethrough and comprising a first region and a second region,
   the first region of the tubular body being positionable adjacent the aneurysm and comprising a plurality of stent members interwoven to form at least one first braid defining a plurality of first region openings,
   the second region of the tubular body located immediately adjacent the first region and comprising at least one second braid, the second braid comprising at least one strand that is formed by at least two stent members from the plurality of stent members,
   wherein the at least one second braid defines a plurality of second region openings,
   at least one of the second region openings being larger than any of the first region openings, and
   wherein the first region openings are sized to restrict passage of blood therethrough to cause stagnation of the aneurysm, and the second region openings are sized to allow substantially uninhibited blood flow therethrough.

2. The stent of claim 1, wherein at least one first region opening has an area of about 0.005 mm2 to about 0.15 mm2.

3. The stent of claim 1, wherein at least one second region opening has an area of about 0.05 mm2 to about 0.3 mm2.

4. The stent of claim 1, wherein at least two members of the first braid are braided together to form the at least one second braid.

5. The stent of claim 1, further comprising a third region comprising at least one third braid having at least one strand formed by at least four stent members, wherein the at least one third braid defines a plurality of third region openings, and at least one of the third region openings being larger than any of the second region openings.

6. The stent of claim 5, wherein the third region is immediately adjacent the second region.

7. The stent of claim 5, wherein at least one third region opening has an area of about 0.05 mm2 to about 0.3 mm2.

8. The stent of claim 1, wherein a therapeutic agent coats at least a portion of the stent.

9. The stent of claim 8, wherein the therapeutic agent comprises a genetic therapeutic agent.

10. The stent of claim 8, wherein the therapeutic agent comprises cellular material.

11. The stent of claim 8, wherein the therapeutic agent comprises a polymer coating.

12. The stent of claim 1, wherein at least a portion of the tubular body is self-expandable.

13. The stent of claim 1, wherein at least a portion of the tubular body is balloon-expandable.

14. The stent of claim 1, wherein at least one portion of the tubular body is self-expandable and another portion of the tubular body is balloon-expandable.

* * * * *